United States Patent [19]

Nishimura et al.

[11] Patent Number: 4,804,750

[45] Date of Patent: Feb. 14, 1989

[54] PRODUCTION OF WATER-SOLUBLE CHITIN-OLIGOMERS BY PARTIAL HYDROLYSIS OF CHITIN

[75] Inventors: Tatsumi Nishimura, Shimizu; Eiichi Eto, Numazu; Toyofumi Yamada, Fujikawa, all of Japan

[73] Assignee: Ihara Chemical Industry Co., Ltd., Tokyo, Japan

[21] Appl. No.: 940,358

[22] Filed: Dec. 11, 1986

[30] Foreign Application Priority Data

Dec. 11, 1985 [JP] Japan ................................ 60-278688

[51] Int. Cl.$^4$ .......................... C08B 37/08; C08L 1/00
[52] U.S. Cl. ..................................... 536/20; 536/55.2; 536/124; 106/203
[58] Field of Search ....................... 536/20, 55, 2, 124, 536/53

[56] References Cited

U.S. PATENT DOCUMENTS

| | | | |
|---|---|---|---|
| 3,989,535 | 11/1976 | Capozza | 536/53 |
| 4,424,346 | 1/1984 | Hall et al. | 536/20 |
| 4,436,731 | 3/1984 | Maltz | 536/20 |
| 4,532,321 | 7/1985 | Castle et al. | 536/20 |

FOREIGN PATENT DOCUMENTS 2357645 3/1978 France.

OTHER PUBLICATIONS

Journal of Chemical Soc., section C, 1970, pp. 1654–1655, "The Preparation of Chitin Oligosaccharides".

Primary Examiner—Ronald W. Griffin
Attorney, Agent, or Firm—Oblon, Fisher, Spivak, McClelland & Maier

[57] ABSTRACT

Tetra-N-acetyl-chitotetraose, penta-N-acetylchitopentaose and hexa-N-acetyl-chitohexaose, ones of the water-soluble chitin-oligomers, may be obtained in improved yields, when finely ground chitin is quickly and intimately mixed with a concentrated hydrohalogenic acid containing a particular proportion of the hydrogen halide per a unit quantity of the chitin under the irradiation with ultrasonic waves and also under the agitation by mechanical stirrer, followed by hydrolyzing the chitin in the resulting homogeneous mixture comprising the chitin and the concentrated hydrohalogenic acid while said homogeneous mixture is further continuously irradiated with the ultrasonic waves and also agitated by the mechanical stirrer. From the aqueous phase of the hydrolyzed reaction mixture are recovered the desired water-soluble chitin-oligomers which are each useful as an immunopotentiating, antitumor agent or antifungal, antibacterial agent.

6 Claims, No Drawings

PRODUCTION OF WATER-SOLUBLE CHITIN-OLIGOMERS BY PARTIAL HYDROLYSIS OF CHITIN

SUMMARY OF THE INVENTION

This invention relates to a process for the production of tetra-N-acetyl-chitotetraose, penta-N-acetyl-chitopentaose and hexa-N-acetyl-chitohexaose in improved yields, by partial hydrolysis of chitin. These chitin-oligomers are each useful as an immunopotentiating agent for enhancing the immune response in mammalian animals, including man, against the bacterial and fungal infections and also against the growth of tumors.

BACKGROUND OF THE INVENTION

We, the present inventors, previously have found that a water-soluble chitin-oligomer or chitin-oligosaccharide selected from di-N-acetyl-chitobiose, tri-N-acetyl-chitotriose, tetra-N-acetyl-chitotetraose, penta-N-acetyl-chitopentaose, hexa-N-acetyl-chitohexaose and hepta-N-acetyl-chitoheptaose is useful as the antibacterial and antifungal agents and also as the antitumor agent owing to the immunopotentiating activity of these water-soluble chitin-oligomers when administered intraperitoneally, intravenously or orally to man (see Japanese patent applications Nos. 252761/84 and 50618/85; U.S. patent application Ser. No. 800,774 and European patent application No. 85 308687).

These chitin-oligomers are represented by a general formula

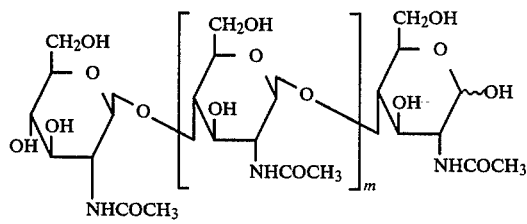

wherein m is zero for di-N-acetyl-chitobiose, m is 1 for tri-N-acetyl-chitotriose, m is 2 for tetra-N-acetyl-chitotetraose, m is 3 for penta-N-acetyl-chitopentaose, m is 4 for hexa-N-acetyl-chitohexaose and m is 5 for hepta-N-acetyl-chitoheptaose. Amongst these chitin-oligomers, tetra-N-acetyl-chitotetraose, penta-N-acetyl-chitopentaose and hexa-N-acetyl-chitohexaose are most preferred owing to their higher immunopotentiating activities than those of the other chitin-oligomers. These water-soluble chitin-oligomers may be produced by partial hydrolysis of chitin, along with a larger quantity of N-acetylglucosamine which is the monomeric unit of the chitin. Chitin is readily available as chitin materials occur in large quantities in nature, for example, in the outer shells of Crustacea such as crabs and lobsters, and also in the shells of insects and the cell walls of various kinds of microorganisms.

It is known that chitin is insoluble in water, organic solvents and aqueous alkali metal hydroxide solutions and that chitin is less wettable by water and is somewhat resistant to alkalis and diluted acids. It is also known that when chitin has been completely hydrolyzed by reacting with a concentrated mineral acid such as concentrated hydrochloric acid for a prolonged reaction time, it can ultimately be converted into glucosamine and acetic acid, with formation of N-acetyl-glucosamine as one of the intermediate products. Besides, it is known that chitin is substantially not hydrolyzable with a diluted aqueous hydrochloric acid in a reasonable reaction time.

For the production of the above-mentioned chitinoligomers from the chitin, a method is known, which comprises adding slowly and gradually a finely ground chitin in small portions into a volume of a concentrated hydrochloric acid in such a way that each small portion of the chitin as added is each time dispersed well in the volume of the concentrated hydrochloric acid used, until the total quantity of the finely ground chitin used can be dispersed in the hydrochloric acid, with requiring a long time for the formation of such dispersion containing the total quantity of the fine chitin particles dispersed in the acid, and then effecting the hydrolysis of the chitin in the resulting dispersion (the reaction mixture of the chitin with the concentrated hydrochloric acid) at an elevated temperature of about 35° C. to 40° C., and subsequently neutralizing the hydrolyzed reaction mixture with aqueous sodium hydroxide, followed by filtering the neutralized reaction mixture, de-salting the resulting filtrate solution containing the soluble hydrolysis products of chitin, recovering the chitin-oligomers from the de-salted filtrate solution and separating chromatographically the chitin-oligomers from each other, on a column of a gelfiltration agent such as Sephadex LH 20 (a product of Pharmacia Fine Chemical Co., Sweden) (see the "Journal of the Chemical Society" 1970, pp. 1654–1655). We have after-tested this known method and have found that with this known method, it is required that the finely ground chitin of the aforesaid nature should be carefully and slowly admixed in small portions with the concentrated hydrochloric acid, with needing a long time for mixing well the fine chitin particles with the acid, as, otherwise, undissolved small lumps of the chitin powder would remain without being wetted by and mixed with the hydrochloric acid agent. Even if a mixture of the chitin powder with the concentrated hydrochloric acid can occasionally have been obtained through severe mixing of the chitin powder with a proper volume of the concentrated hydrochloric acid, the mixture so obtained is usually in the form of a pretty stiff dough-like mass which is not agitatable by means of a mechanical stirrer. In addition, if the volume of the concentrated hydrochloric acid used per a given quantity of the chitin powder is increased excessively for the purpose of enabling the chitin powder to be well mixed with and dispersed in the hydrochloric acid and give a more fluid and agitatable dispersion or mixture, the hydrolysis of chitin can proceed excessively to give increased yields of glucosamine and N-acetylglucosamine which are not desired in the present invention, and also give decreased yields of the tetra-N-acetyl-chitotetraose, penta-N-chitopentaose and hexa-N-acetyl-chitohexaose which are most desired to be recovered in the present invention.

According to the known method described in the above-mentioned "Journal of the Chemical Society" 1970, pp. 1654–1655, an experiment was made, where finely ground chitin (100 g) was slowly added to with stirring and then hydrolyzed with 200 ml of a concentrated hydrochloric acid for totally 3 hours, the hydrolyzed reaction mixture was neutralized with 50% aqueous sodium hydroxide and filtered, followed by de-salting the neutral filtrate solution (300 ml) on a column of Sephadex G-25 and freeze-drying the resulting desalted fractions of the effluent to yield of a mixture of N-acetylglucosamine and its oligosaccharides with degrees of polymerisation of 2 to 6, namely the di-N-acetyl-chitobiose, tri-N-acetyl-chitotriose, tetra-N-acetyl-chitotetraose, penta-N-acetylchitopentaose and hexa-N-acetyl-chitohexaose (hereinafter sometime abbreviated as NACOS-2-, NACOS-3, NACOS-4, NACOS-5 and NACOS-6, respectively), and where said mixture of N-acetylglucosamine and NACOS-2 to NACOS-6 was obtained only in a poor yield of 6.5 g from 100 g of the chitin material charged. In this experiment, said mixture (6.5 g) of N-acetylglucosamine and NACOS-2 to NACOS-6 was then chromatographed on a column of Sephadex LH 20 to give 0.13 g of NACOS-6, 0.3 g of NACOS-5, 0.47 g of NACOS-4, 0.81 g of NACOS-3, 0.78 g of NACOS-2 and 0.70 g of N-acetylglucosamine (NACOS), respectively. Thus, according to the aforesaid known method, the total yields of hexa-N-acetyl-chitohexaose (NACOS-6), penta-N-acetyl-chitopentaose (NACOS-5) and tetra-N-acetyl-chitotetraose (NACOS-4) recovered from chitin were considerably smaller than the total yields of the lower chitin-oligomers such as di-N-acetyl-chitobiose (NACOS-2) and tri-N-acetyl-chitotriose (NACOS-3) and were difficult to be further increased.

According to the above-mentioned known method, it is required that the powder (100 g) of the starting chitin material is so added in small portions slowly and gradually into the volume (200 ml) of the concentrated hydrochloric acid used, that the resulting mixture is always kept to be in the form of a uniform liquid dispersion which is agitatable by means of a mechanical stirrer, and due to this, a considerably long time must be taken to complete even the mixing of the total quantity of the chitin powder used, with the concentrated hydrochloric acid agent. Thus, then it is considered that the first portions of the whole chitin powder which have been added at first into the concentrated hydrochloric acid at the early stage of mixing the chitin powder with the hydrochloric acid can be exposed to and reacted with the excessive quantity of the hydrogen chloride present in the resulting dispersion (the reaction mixture) for an improperly prolonged time and hence can be hydrolyzed to such excessive extents as to produce predominantly N-acetylglucosamine and even glucosamine as the ultimate hydrolysis products of chitin, whereas the latter portions of the whole chitin powder which are added later into the mixture at the later stage of mixing the chitin powder with the hydrochloric acid are not hydrolyzed to such excessive extents as above. For these reasons, it is considered that the above-mentioned known method is difficult to provide better yields of the desired tetra-N-acetyl-chitotetraose, penta-N-acetyl-chitopentaose and hexa-N-acetyl-chitohexaose recovered. When an increased volume of a diluted hydrochloric acid has been mixed with the chitin powder with an intention of giving a more fluid and agitatable mixture, the hydrolysis of chitin cannot proceed to a substantial extent in a reasonable reaction time.

DETAILED DESCRIPTION OF THE INVENTION

We, the present inventors, have made extensive researches in an attempt to provide such a new process for the production of NACOS-4, NACOS-5 and NACOS-6 by partial hydrolysis of chitin, which can be operated efficiently and smoothly in a reasonable reaction time and which can give improved and favorable yields of these desired chitin-oligomers from a given quantity of the chitin material charged, so that the yields of these desired chitin-oligomers can be recovered in improved yields, as compared to the above-mentioned known prior art method. As a result of our researches, we have now found that a quantity in the order of 100 g of the chitin powder can intimately be mixed quickly with a relatively small volume in the order of 200 ml of a concentrated aqueous hydrochloric acid, when the chitin powder is added at once to the concentrated hydrochloric acid under agitating by means of a mechanical stirrer and concurrently the whole of the chitin powder and the concentrated hydrochloric acid under agitating is irradiated with utlrasonic waves, and accordingly that a homogeneous dispersion of the fine chitin particles intimately mixed and dispersed in the concentrated hydrochloric acid can thus be prepared quickly by admixing the whole chitin powder at once with the concentrated hydrochloric acid under agitation by means of a mechanical stirrer and under irradiation with ultrasonic waves, in combination, without needing such troublesome operation as involved in the prior art method that the chitin powder must be added in small portions slowly and gradually into the hydrochloric acid with taking a long time and with inevitably bringing about the excessive hydrolysis of some portions of the chitin as described hereinbefore. We have also found that once when the homogeneous dispersion of the fine chitin particles dispersed in the concentrated hydrochloric acid has been formed under the agitation by the mechanical stirrer and under the actions of the ultrasonic waves irradiated, the hydrolysis of the chitin in the dispersion, namely in the reaction mixture as formed can subsequently proceed smoothly in a reasonable reaction time, as long as said dispersion or reaction mixture continues to be agitated by the mechanical stirrer while being concurrently irradiated with the ultrasonic waves, and further that then, all the fine particles of the chitin dispersed in the concentrated hydrochloric acid can concurrently react with the concentrated hydrochloric acid from the start and can evenly be subjected to the hydrolyzing reaction, so that it does not happen that any portions of the chitin material can be hydrolyzed to more excessive extents than the other portions of the chitin material existing in the reaction mixture where the hydrolyzing reaction proceeds. We have found that generally, any concentrated aqueous hydrohalogenic acid may be employed for hydrolyzing the chitin material in the above-mentioned process. From our further researches, moreover, we have now found that when the chitin powder has been intimately mixed with and dispersed in an amount of a concentrated hydrohalogenic acid containing 1.5 mol to 6 mol of the hydrogen halide per 100 g of the chitin as initially charged, under the agitation by means of mechanical stirrer and under the irradiation with ultrasonic waves, and when the homogeneous dispersion or reaction mixture of the chitin particles in the concentrated hydrohalogenic acid as once formed is then continuously agitated by the mechanical stirrer while being irradiated with the ultrasonic waves, the hydrolysis of the chitin can proceed smoothly to such extents that the total yields of the desired tetra-N-acetyl-chitotetraose (NACOS-4), penta-N-acetyl-chitopentaose (NACOS-5) and hexa-N-acetyl-chitohexaose (NACOS-6) as produced and recovered from the given quantity of the chitin can be improved remarkably, as compared to when the particular proportion chosen as above of the hydrogen halide per 100 g. of the chitin is not employed or when the reaction mixture is not agitated by means of the mechanical stirrer under the irradiation with the ultrasonic waves. Based on these findings of ours, this invention has been made.

According to a first aspect of this invention, therefore, there is provided a process for the production of tetra-N-acetyl-chitotetraose, penta-N-acetyl-chitopentaose and hexa-N-acetyl-chitohexaose, these chitinoligomers being represented by the general formula (I)

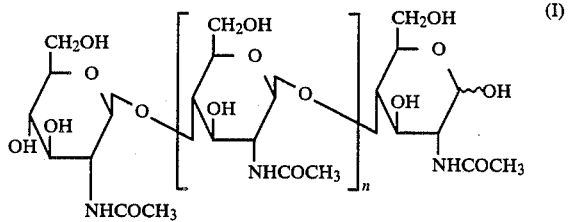

wherein n is 2 for the tetra-N-acetyl-chitotetraose, n is 3 for the penta-N-acetyl-chitopentaose, and n is 4 for the hexa-N-acetyl-chitohexaose, which comprises adding finely ground chitin at once to and intimately mixing said chitin with an amount of a concentrated hydrohalogenic acid containing 1.5 mol to 6 mol of the hydrogen halide per 100 g of the chitin initially charged, while being irradiated with ultrasonic waves and also agitated by means of mechanical stirrer, to form a homogeneous mixture of the fine chitin particles with the concentrated hydrohalogenic acid, and then hydrolyzing the chitin with the concentrated hydrohalogenic acid, while the resulting homogeneous reaction mixture comprising the chitin and the concentrated hydrohalogenic acid is further continuously irradiated with the ultrasonic waves and also agitated by means of the mechanical stirrer.

According to a further aspect of this invention, there is provided a process for the production of tetra-N-acetyl-chitotetraose, penta-N-acetyl-chitopentaose and hexa-N-acetyl-chitohexaose, these chitin-oligomers being represented by the general formula (I)

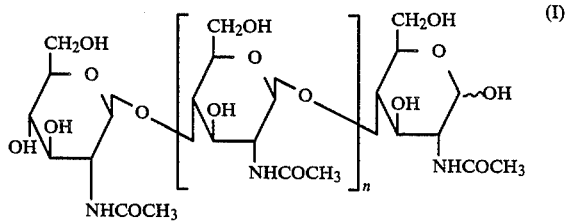

wherein n is 2 for the tetra-N-acetyl-chitotetraose, n is 3 for the penta-N-acetyl-chitopentaose, and n is 4 for the hexa-N-acetyl-chitohexaose, which comprises the steps of:

(i) adding finely ground chitin at once to and intimately mixing said chitin with an amount of a concentrated hydrohalogenic acid containing 1.5 mol to 6 mol of the hydrogen halide per 100 g of the chitin initially charged, while being irradiated with ultrasonic waves and also agitated by means of mechanical stirrer, to form a homogeneous mixture of the fine chitin particles with the concentrated hydrohalogenic acid, (ii) then hydrolyzing the chitin with the concentrated hydrohalogenic acid, while the resulting homogeneous reaction mixture comprising the chitin and the concentrated hydrohalogenic acid is further continuously irradiated with the ultrasonic waves and also agitated by means of the mechanical stirrer, (iii) continuing the reaction of hydrolyzing the chitin under the irradiation with the ultrasonic waves and under the agitation by the mechanical stirrer, until 40% by weight or more of the chitin charged have been depolymerized hydrolytically and dissolved into the aqueous phase of the reaction mixture, with formation of N-acetylglucosamine, di-N-acetyl-chitobiose, tri-N-acetyl-chitotriose, tetra-N-acetyl-chitotetraose, penta-N-acetylchitopentaose, hexa-N-acetyl-chitohexaose and hepta-N-acetyl-chitoheptaose which are soluble in water, and (iv) recovering from the aqueous phase of the hydrolyzed reaction mixture the tetra-N-acetyl-chitotetraose, penta-N-acetyl-chitopentaose and hexa-N-acetyl-chitopentaose, either in mixture or singly.

This process according to the second aspect of this invention may be so modified that the acid used is a concentrated hydrochloric acid and the step (iii) of continuing the reaction of hydrolyzing the chitin under the irradiation with ultrasonic waves and under the mechanical agitation is followed by the step (iv) of recovering the tetra-N-acetyl-chitotetraose, penta-N-acetyl-chitopentaose and hexa-N-acetyl-chitohexaose, which includes such stages wherein (a) the whole, hydrolyzed reaction mixture after the completion of the hydrolyzing reaction is neutralized with aqueous sodium hydroxide, aqueous pottasium hydroxide, aqueous sodium or potassium carbonate or aqueous sodium or potassium hydrogen carbonate, (b) the neutralized reaction mixture is filtered to remove the insoluble residue and afford the neutral, aqueous filtrate containing N-acetylglucosamine, the watersoluble chitin-oligomers and the sodium chloride as formed, (c) the neutral aqueous filtrate solution is then desalted, (d) the resulting de-salted aqueous solution containing the N-acetylglucosamine and the water-soluble chitin-oligomers is concentrated or dried to give a concentrate or solid mixture containing the N-acetylglucosamine and the water-soluble chitin-oligomers, and (e) the concentrate or solid mixture so obtained is chromatographed, for example, on a column of a gel-filtration agent or by a high pressure liquid chromatography.

The chitin which is used as the starting material in the process of this invention is a naturally occurring material available in large quantities and is composed of β-1,4-linked polysaccharides of N-acetylglucosamine. A purified or partially purified product of chitin may be obtained, for example, from the outer shells of crabs and lobsters and may suitably be employed in the present process.

Suitable examples of the hydrohalogenic acid used in the process of this invention include hydrochloric acid and hydrobromic acid. The hydrohalogenic acid as used in the present process is of a concentrated aqueous form, and the concentration of the hydrogen halide in the acid may be in a range of 10N to 12N, namely in a range of 10 mol to 12 mol of the hydrogen halide. When a concentrated hydrochloric acid is used, a concentrated hydrochloric acid containing more than 10N of the hydrogen chloride is preferred. When another hydrohalogenic acid is employed, the concentration of the hydrogen halide present therein is preferred to be higher than 10N. If a hydrohalogenic acid containing the hydrogen halide at a lower concentration than 10N is employed, the hydrolysis of chitin cannot proceed smoothly to the desirably high extent in a reasonable reaction time and hence the desired chitin-oligomers cannot be obtained in favorably high yields as desired. If a mineral acid other than the hydrohalogenic acid, for example, sulfuric acid is employed, the hydrolysis of chitin cannot proceed smoothly to the desirably high extent in a reasonable reaction time, so that the desired chitin-oligomers cannot be obtained in favorably high yields, too.

In the process of this invention, the amount of the concentrated hydrohalogenic acid to be reacted with the chitin is necessary to be such an amount which provides or contains 1.5 mol to 6 mol of the hydrogen halide per 100 g (dry weight) of the chitin as initially charged. Thus, the quantity of the hydrogen halide present in the reaction mixture for hydrolyzing the chitin should be in a range of 1.5 mol to 6 mol per 100 g of the chitin as added and should preferably be in a range of 2 mol to 5 mol per 100 g of the chitin. If the quantity of the hydrogen halide used is less than 1.5 mol per 100 g of the chitin as added, the hydrolysis of chitin cannot proceed to the desirably high extent in a reasonable reaction time, so that the desired chitin-oligomers (NACOS-4 to NACOS-6) cannot be recovered in the improved yields as desired. While, if the quantity of the hydrogen halide used is higher than 6 mol per 100 g of the chitin as added, the hydrolysis of chitin can proceed to undesirably excessive extents, with a consequence that the desired chitin-oligomers again can be recovered in the poorer yields.

In the process of this invention, the hydrolyzing reaction is carried out at a temperature of 0° C. to 40° C., particularly 20° C. to 35° C., preferably 30°-40° C. and for a reaction time of 2 hours to 3 hours, while the reaction mixture comprising the chitin and the concentrated hydrohalogenic acid is irradiated with the ultrasonic waves and also agitated by the stirrer, so that the reaction mixture undergoes the hydrolyzing reaction under the actions of the ultrasonic waves and the mechanical agitation. Although the reaction mixture comprising the finely ground chitin and the concentrated hydrohalogenic acid is at first in the form of a very viscous dough-like mass at a very initial stage of the reaction even with being exposed to the actions of the ultrasonic waves, said reaction mixture can soon change into a fluid and easily agitatable, homogenous mixture or dispersion when the reaction mixture is further exposed to the actions of the ultrasonic waves and the mechanical agitation by the stirrer continuously for about 10 to 30 minutes. For instance, said mixture can have became a fluid and easily agitatable liquid dispersion having a viscosity of 10,000 poises or less when it has been irradiated with the ultrasonic waves for about 2 hours under the mechanical agitation by the stirrer. After this, the hydrolysis of chitin can proceed efficiently and smoothly to such extents that the desired chitin-oligomers (NACOS-4 to NACOS-6) can be recovered in the improved yields from the aqueous phase of the reaction mixture after completion of the hydrolyzing reaction. During the hydrolyzing reaction, the reaction mixture is agitated mechanically by means of conventional, mechanical stirrer(s) while being irradiated with the ultrasonic waves which also exert some agitating effect to said reaction mixture.

The mechanical stirrer available in the present process is a conventional one fitted with propeller, screw or helical blade.

The ultrasonic waves to be irradiated to the reaction mixture may be of relatively lower frequencies of from 10 K Hz to 100 K Hz and may also be of relatively higher frequencies of from 150 K Hz to 200 K Hz. The strength or power of the ultrasonic waves may be in a range of 10 Watts to 600 Watts. When the frequencies of the ultrasonic waves used are chosen in the above-mentioned ranges with appropriately adjusting the total strength of the ultrasonic waves to proper one, the mixture of the chitin with the concentrated hydrohalogenic acid can change into a fluid and easily agitatable, homogenous mixture so that the hydrolysis of chitin can proceed efficiently and smoothly to such extents to give the improved yields of the desired chitin-oligomers. For instance, when the process of this invention is worked in a small scale for the production of the desired water-soluble chitin-oligomers, a commercially available, ultrasonic washing apparatus capable of generating the ultrasonic waves of 20 to 50 K Hz frequencies at a power of 20 to 600 Watts may be employed to irradiate the reaction mixture with the ultrasonic waves. When the reaction mixture continues to undergo the ultrasonic wave actions, the temperature in the reaction mixture is usually likely to raise, and then the reaction mixture may be cooled, if necessary, to avoid any excessive raising of the temperature.

In the process of this invention, normally, the hydrolyzing reaction is continued under the actions of the ultrasonic waves and the mechanical agitation, until 40% by weight or more of the chitin initially charged have been depolymerized hydrolytically and dissolved in the aqueous phase of the reaction mixture, and preferably until 40% to 80% by weight of the chitin have been dissolved in the aqueous phase of the reaction mixture. The hydrolyzing reaction may be stopped an appropriate reaction time as determined by simple, preliminary tests which are carried out to decide a best reaction time which can give best improved yields of the desired chitin-oligomers recovered from the aqueous phase of the reaction mixture after the completed reaction.

Usually, good results may be obtained by continuing the hydrolyzing reaction for a reaction time of 2 to 3 hours. If the reaction time exceeds 3 hours, it is likely that the undesired, lower chitin-oligomers are produced in increased proportions. And, if more than 80% by weight of the chitin initially added has been depolymerized and dissolved in the aqueous phase of the reaction mixture being hydrolyzed, it is likely that the recovered total yields of the desired tetra-N-acetyl-chitotetraose, penta-N-acetyl-chitopentaose and hexa-N-acetyl-chitohexaose decrease to a value smaller than the best total yields of the desired chitin-oligomer which would be achivable by the process of this invention.

In the process of this invention, the irradiation of the reaction mixture with the ultrasonic waves serves to assist the mechanical stirrer in mixing the fine chitin particles well and intimately with the concentrated hydrohalogenic acid and also to render the resulting dispersion or mixture fluid and easily agitatable. In addition, it is considered that the irradiation with the ultrasonic waves can have further advantageous effects that the hydrohalogenic acid reagent can be promoted to penetrate into the solid fine particles of the finely ground chitin to access to and attack hydrolytically the chitin molecules existing within every particles of the chitin, and the chitin particles having somewhat reacted with the acid can be collaped into more finer particles, with making the mixture more homogeneous and hence promoting the hydrolyzing reaction and thus enhancing the extent of hydrolysis of the chitin material obtainable in a given reasonable reaction time, with the consequence, that the total proportions of NACOS-4, NACOS-5 and NACOS-6 as formed in the whole hydrolysis products of chitin can be increased, as compared to when the hydrolyzing reaction would be carried out in the absence of the irradiating ultrasonic waves.

After completion of the hydrolyzing reaction, the reaction mixture containing all the hydrolysis products of chitin is neutralized with aqueous sodium or potassium hydroxide, aqueous sodium or potassium carbonate or aqueous sodium or potassium hydrogen carbonate. The neutralized reaction mixture is then filtered to remove therefrom the insoluble residue comprising the little depolymerized chitin materials and some quantity of the unreacted chitin material and to afford the aqueous filtrate solution containing N-acetylglucosamine, the water-soluble chitin-oligomers, including hepta-N-acetylchitoheptaose (NACOS-7), and the sodium chloride or halide as formed.

For recovery of the desired water-soluble chitinoligomers (NACOS-4 to NACOS-6), the neutral aqueous filtrate so obtained is de-salted by a gel-filtration agent such as Sephadex G-25 or by an electric dialysis apparatus fitted with anion-permiable anion-exchange membranes and cation-permeable cation-exchange membrane, and the resulting de-salted solution containing N-acetylglucosamine and the water-soluble chitin-oligomers (NACOS-2 to NACOS-7) is then concentrated or dried to give a concentrate or a solid mixture comprising the N-acetylglucosamine and the chitin-oligomers (NACOS-2 to NACOS-7). The concentrate or solid mixture obtained may subsequently be chromatographed, for example, on a column of a gel-filtration agent such as Sephadex LH 20, or by a high pressure liquid chromatography on a column of $\mu$-Bondapack CH as developed with methylnitrile-water (70:30), so that the desired tetra-N-acetyl-chitotetraose (NACOS 4), penta-N-acetyl-chitopentaose (NACOS-5) and hexa-N-acetyl-chitohexaose (NACOS-6) are isolated, either in mixture or singly, with being separated from the by-produced N-acetylglucosamine, di-N-acetyl-chitobiose (NACOS-2), tri-N-acetyl-chitotriose (NACOS-3) and hepta-N-acetyl-chitoheptaose (NACOS-7).

When the neutralized aqueous filtrate separated as above from the hydrolyzed reaction mixture is de-salted by passing this filtrate through a column of a gel-filtration agent such as Sephadex G-25, the sodium chloride or halide present in said neutralized filtrate can be removed by absorption into the gel-filtration agent, and concurrently larger proportions of the N-acetylglucosamine, di-N-acetyl-chitobiose and tri-N-acetyl-chitotriose, as well as small proportions of the tetra-N-acetyl-chitotetraose, penta-N-acetyl-chitopentaose and hexa-N-acetyl-chitohexaose contained in said neutralized filtrate can also be absorbed into the gel-filtration agent used. So, the effluent coming from the column of the gel-filtration agent is then containing larger proportions of the desired tetra-N-acetyl-chitotetraose, penta-N-acetyl-chitopentaose and hexa-N-acetyl-chitohexaose, together with minor proportions of the N-acetyl-glucosamine, di-N-acetyl-chitobiose and tri-N-acetyl-chitotriose.

This invention is now illustrated with reference to the following Examples to which this invention is not limited.

EXAMPLE 1

A finely ground chitin (100 g) having particle size of 16 meshes or less (a purified chitin material as produced from a crab, *Chionoecetes Japonicus*, Rathban, commercially available from Katakura Chikkarin Co., Ltd., Japan) and 400 ml of 12N hydrochloric acid (containing 4.8 mol of the hydrogen chloride) were placed together in a three-necked flask of 1 l capacity. The mixture in the flask was irradiated with ultrasonic waves and also agitated by means of a mechanical stirrer for 15 minutes at a temperature below 30° C. so that the chitin particles were intimately and well mixed with the hydrochloric acid. During this mixing step, the flask containing the mixture of the chitin and the acid had been placed in an apparatus of generating ultrasonic waves (of the frequencies of 48 K Hz, manufactured by Branson Co., U.S.A.), while being irradiated with the ultrasonic waves at the power of 300 Watts. The resulting homogeneous, reaction mixture comprising the chitin and the hydrochloric acid was further agitated by means of the mechanical agitator at temperatures of 40° C. for 2 hours, while the reaction mixture was continuously irradiated with the ultrasonic waves. In this way, the reaction of hydrolyzing the chitin material was effected for the 2 hours. After the reaction was stopped, the hydrolyzed reaction mixture was neutralized to pH 7 with addition of aqueous sodium hydroxide under ice-cooling. The neutralized reaction mixture was filtered to remove the insoluble residue, which was washed with water, dried and weighed. The aqueous filtrate as separated from the neutralized reaction mixture was pooled and then de-salted by passing through a column (a length of 100 cm and a diameter of 10 cm) of a gel-filtration agent, Sephadex G-25 (a product of Pharmacia Fine Chemical Co., Sweden) to effect the gel-filtration according to gel chromatography. The fractions (each 100 ml) of the effluent coming from the Sephadex G-25 column were analyzed by thin layer chromatography on Kieselgel as developed with propanol-water-ammonia. All the effluent fractions which did not contain the chloride anion (as tested by coloration with an aqueous silver nitrate) were collected and combined together.

The combined effluent fractions were freeze-dried to give 36 g of a solid mixture comprising tetra-N-acetyl-chitotetraose (NACOS-4), penta-N-acetyl-chitopentaose (NACOS-5) and hexa-N-acetyl-chitohexaose (NACOS-6), together with minor proportions of N-acetylglucosamine, di-N-acetyl-chitobiose, tri-N-acetyl-chitotriose. This mixture comprising the water-soluble chitin-oligomers was then chromatographed by a high pressure liquid chromatography on a column of $\mu$-Bondapack CH (a product of Waters Company, U.S.A.) as eluted with methylnitrile-water (70:30 by volume), to effect the isolation of the chitin-oligomers from each other, affording 3.10 g of hexa-N-acetylchitohexaose having an $[\alpha]_D$ of $-11.2°$ and a decomposition temperature of 300° C., 7.6 g of penta-N-acetyl-chitopentaose having an $[\alpha]D$ of $-9.0°$ and a decompsition temperature of 304° C.; and 8.1 g of tetra-N-acetyl-chitotetraose having an $[\alpha]_D$ of $-4.2°$ and a decomposition temperature of 299° C.

The degree of hydrolysis of the chitin material as achieved was calculated from the weighed quantity of the recovered insoluble residue (comprising the little depolymerized chitin and the unreacted chitin) and the initial weight of the chitin charged, according to the following equation:

Degree (%) of hydrolysis of chitin =

$$\frac{\text{(Initial weight of chitin)} - \text{(Weight of recovered insoluble residue)}}{\text{(Initial weight of chitin)}} \times 100$$

It was assumed that such a portion of the initial chitin material which is corresponding to the calculated degree (%) of hydrolysis of chitin had been converted into the water-soluble hydrolysis products of chitin. Thus, the calculated degree (%) of hydrolysis of chitin means the rate (in per cent) of conversion of the chitin material into the hydrolysis products by the hydrolyzing reaction. With this assumption, the proportions (in per cent) of the isolated and recovered hexa-N-acetyl-chitohexaose (NACOS-6), penta-N-acetyl-chitopentaose (NACOS-5) and tetra-N-acetylchitotetraose (NACOS-4) were calculated, based on the total weights of all the water-soluble hydrolysis products of chitin.

From further experiments, it was found that the above-mentioned Sephadex G-25 column after the desalting stage of the neutralized reaction mixture had absorbed not only the sodium chloride but also large quantities of the N-acetylglucosamine, di-N-acetyl-chitobiose (NACOS-2) and tri-N-acetyl-chitotriose (NACOS-3), as well as small quantities of NACOS-4, NACOS-5 and NACOS-6.

The test results obtained are summarized in Table 1 given hereinafter.

EXAMPLE 2

The procedure of Example 1 was repeated, except that the amount of the 12N hydrochloric acid used was decreased to 200 ml (containing 2.4 mol of the hydrogen chloride). The test results obtained are summarized in Table 1 hereinafter.

COMPARATIVE EXAMPLE 1

The procedure of Example 2 was repeated, except that the irradiation with the ultrasonic waves was omitted.

The test results obtained are shown in Table 1.

COMPARATIVE EXAMPLE 2

The procedure of Example 1 was repeated, except that the amount of the 12N hydrochloric acid was increased to 600 ml (containing 7.2 mol of the hydrogen chloride).

The test results obtained are shown in Table 1.

TABLE 1

| Examples | Amount of 12 N HCl used | Moles of HCl reacted per 100 g of chitin | Ultrasonic waves | Degree (%) of hydrolysis of chitin |
|---|---|---|---|---|
| Example 1 | 400 ml | 4.8 | Irradiated | 75.0% |
| Example 2 | 200 ml | 2.4 | Irradiated | 48.8% |
| Comparative Example 1 | 200 ml | 2.4 | Not Irradiated | 49.0% |
| Comparative Example 2 | 600 ml | 7.2 | Irradiated | 90.0% |

| Examples | Recovered yield (g) of NACOS-6 (per cent of NACOS-6 in the hydrolysis products of chitin) | Recovered yield (g) of NACOS-5 (per cent of NACOS-5 in the hydrolysis products of chitin) | Recovered yield (g) of NACOS-4 (per cent of NACOS-4 in the hydrolysis products of chitin) | Total yield (g) of recovered NACOS-4, NACOS-5 and NACOS-6 |
|---|---|---|---|---|
| Example 1 | 3.10 g (4.13%) | 7.6 g (10.13%) | 8.1 g (10.8%) | 18.8 g |
| Example 2 | 2.7 g (5.53%) | 6.7 g (13.7%) | 8.3 g (17.01%) | 17.7 g |
| Comparative Example 1 | 0.51 g (1.04%) | 1.5 g (3.10%) | 2.3 g (4.69%) | 4.31 g |
| Comparative Example 2 | 0.85 g (0.94%) | 1.7 g (1.89%) | 1.4 g (1.60%) | 3.95 g |

Notes:
in Table 1 above, NACOS-6 denotes hexa-N—acetyl-chitohexaose; NACOS-5 denotes penta-N—acetyl-chitopentaose; and NACOS-4 denotes tetra-N—acetyl-chitotetraose.

From the test results of Table 1 above, it is generally seen that the Examples 1–2 according to this invention can recover the desired water-soluble chitin-oligomers of NACOS-4, NACOS-5 and NACOS-6 in remarkably improved yields, as compared to the Comparative Examples 1–2, where the ultrasonic waves were not irradiated or the proportion of the hydrogen chloride as reacted per 100 g of chitin was falling outside the particular range specified according to this invention. More particularly, the comparison of the test results of Example 2 with those of Comparative Example 1 reveals that the irradiation with ultrasonic waves according to this invention can increase the total proportions of the water-soluble NACOS-4, NACOS-5 and NACOS-6 as formed among the whole, water-soluble hydrolysis products of chitin, including N-acetylglucosamine and chitin-oligomers as formed, as compared to the Comparative Example 2 where the ultrasonic wave irradiation was omitted, though the degree (%) of hydrolysis of chitin does not substantially change between the presence and the absence of the effects of the ultrasonic wave irradiation. Besides, the comparison of the test results of Example 1 with those of the Comparative Example 2 reveals that when the proportion of the hydrogen chloride as reacted per 100 g of chitin exceeded the upper limit of 6 mol as specified according to this invention, the degree (%) of hydrolysis of chitin can increase excessively so that the recovered yields of the NACOS-4, NACOS-5 and NACOS-6 were decreased markedly.

What we claim is:

1. A process for the production of tetra-N-acetyl-chitotetraose, penta-N-acetyl-chitopentaose and hexa-N-acetyl-chitohexaose, these chitin-oligomers being represented by the general formula (I)

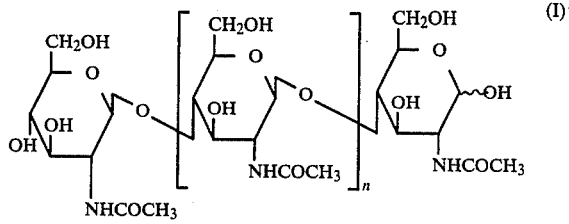

wherein n is 2 for the tetra-N-acetyl-chitotetraose, n is 3 for the penta-N-acetyl-chitopentaose, and n is 4 for the hexa-N-acetyl-chitohexaose, which comprises adding finely ground chitin at once to and intimately mixing said chitin with an amount of a concentrated hydrohalogenic acid containing 1.5 mol to 6 mol of the hydrogen halide per 100 g of the chitin initially charged, while being irradiated with ultrasonic waves and also agitated by means of mechanical stirrer, to form a homogeneous mixture of the fine chitin particles with the concentrated hydrohalogenic acid, and then hydrolyzing the chitin with the concentrated hydrohalogenic acid, while the resulting homogeneous reaction mixture comprising the chitin and the concentrated hydrohalogenic acid is further continuously irradiated with the ultrasonic waves and also agitated by means of the mechanical stirrer.

2. A process as claimed in claim 1, for the production of tetra-N-acetyl-chitotetraose, penta-N-acetyl-chitopentaose and hexa-N-acetyl-chitohexaose, which comprises the steps of:
(i) adding finely ground chitin at once to and intimately mixing said chitin with an amount of a concentrated hydrohalogenic acid containing 1.5 mol to 6 mol of the hydrogen halide per 100 g of the chitin initially charged, while being irradiated with ultrasonic waves and also agitated by means of mechanical stirrer, to form a homogeneous mixture of the fine chitin particles with the concentrated hydrohalogenic acid,
(ii) then hydrolyzing the chitin with the concentrated hydrohalogenic acid, while the resulting homogeneous reaction mixture comprising the chitin and the concentrated hydrohalogenic acid is further continuously irradiated with the ultrasonic waves and also agitated by means of the mechanical stirrer,
(iii) continuing the reaction of hydrolyzing the chitin under the irradiation with the ultrasonic waves and under the agitation by the mechanical stirrer, until 40% by weight or more of the chitin charged have been depolymerized hydrolytically and dissolved into the aqueous phase of the reaction mixture, with formation of N-acetylglucosamine, di-N-acetyl-chitobiose, tri-N-acetyl-chitotriose, tetra-N-acetyl-chitotetraose, penta-N-acetyl-chitopentaose, hexa-N-acetyl-chitohexaose and hepta-N-acetyl-chitoheptaose which are soluble in water, and
(iv) recovering from the aqueous phase of the hydrolyzed reaction mixture the desired tetra-N-acetyl-chitotetraose, penta-N-acetyl-chitopentaose and hexa-N-acetyl-chitohexaose, either in mixture or singly.

3. A process as claimed in claim 1 or 2, in which the hydrohalogenic acid used is a 10N to 12N hydrochloric acid and the chitin is hydrolyzed with a concentrated hydrochloric acid containing the hydrogen chloride at a concentration of 10N to 12N at a temperature of 35° C. to 40° C. for a time of about 2 hours to 3 hours.

4. A process as claimed in claim 1 or 2, in which the mixture comprising the chitin and the concentrated hydrochloric acid is continuously irradiated with ultrasonic waves of frequencies of 10 K Hz to 200 K Hz and also agitated by mechanical stirrer.

5. A process as claimed in claim 1 or 2, in which the reaction of hydrolyzing the chitin is effected under the irradiation with ultrasonic waves and under the mechanical agitation by stirrer until 40% to 80% by weight of the chitin initially charged have been depolymerized hydrolytically and dissolved in the aqueous phase of the reaction mixture.

6. A process as claimed in claim 2, in which the acid used is a concentrated hydrochloric acid and the step of recovering the tetra-N-acetyl-chitotetraose, penta-N-acetyl-chitopentaose and hexa-N-acetylhexaose from the aqueous phase of the hydrolyzed reaction mixture includes stages where (a) the whole, hydrolyzed reaction mixture after the completed reaction is neutralized with aqueous sodium or potassium hydroxide, aqueous sodium or potassium carbonate or aqueous sodium or potassium hydrogen carbonate, (b) the neutralized reaction mixture is filtered to remove the insoluble residue and afford the neutral, aqueous filtrate containing N-acetylglucosamine, the water-soluble chitin-oligomers and the sodium chloride as formed, (c) the neutral aqueous filtrate obtained is then desalted, (d) the resulting de-salted aqueous solution containing the N-acetylglucosamine and the water-soluble chitin-oligomers is concentrated or dried to give a concentrate or solid mixture containing the N-acetylglucosamine and the chitin-oligomers, and (e) the concentrate or solid mixture so obtained is chromatographed on a column of a gel-filtration agent or by a high pressure liquid chromatography, to obtain the tetra-N-acetyl-chitotetraose, penta-N-acetylchitopentaose and hexa-N-acetyl-chitohexaose, either in mixture or singly.

* * * * *